United States Patent
Gamache et al.

(10) Patent No.: US 7,219,024 B2
(45) Date of Patent: May 15, 2007

(54) MATERIAL ANALYSIS INCLUDING DENSITY AND MOISTURE CONTENT DETERMINATIONS

(75) Inventors: Ronald W. Gamache, East Greenbush, NY (US); Richard Hosterman, Buskirk, NY (US); Sarah Pluta, Clifton Park, NY (US)

(73) Assignee: TransTech Systems, Inc., Schenectady, NY (US)

( * ) Notice: Subject to any disclaimer, the term of this patent is extended or adjusted under 35 U.S.C. 154(b) by 7 days.

(21) Appl. No.: 11/127,391

(22) Filed: May 12, 2005

(65) Prior Publication Data

US 2005/0267700 A1    Dec. 1, 2005

Related U.S. Application Data

(60) Provisional application No. 60/574,680, filed on May 26, 2004.

(51) Int. Cl.
*G01R 27/00* (2006.01)
(52) U.S. Cl. .................... 702/65; 702/182; 324/663
(58) Field of Classification Search .................. 702/57, 702/65, 75, 85, 104, 182–183, 186; 324/663, 324/654, 691
See application file for complete search history.

(56) References Cited

U.S. PATENT DOCUMENTS

| | | |
|---|---|---|
| 3,400,331 A | 9/1968 | Harris |
| 3,671,857 A | 6/1972 | Bergmanis et al. |
| 3,694,742 A | 9/1972 | Bergmanis et al. |
| 3,781,672 A | 12/1973 | Maltby et al. |
| 3,784,905 A | 1/1974 | Blackwell |
| 3,882,381 A | 5/1975 | Gregory |
| 3,967,912 A | 7/1976 | Parker |
| 4,099,118 A | 7/1978 | Franklin et al. |
| 4,389,136 A | 6/1983 | Fehrenbach |
| 4,433,286 A | 2/1984 | Capots |
| 4,468,610 A | 8/1984 | Hanson |
| 4,604,612 A | 8/1986 | Watkins et al. |

(Continued)

FOREIGN PATENT DOCUMENTS

FR    2593200 A1    7/1987

OTHER PUBLICATIONS

Atkins, Ronald T. et al., "Soil Moisture Determinations Using Capacitance Probe Methodology," U.S. Army Corps of Engineers, Cold Regions Research & Engineering Laboratory, Special Report 98-2, Jan. 1998, pp. 1-43.

(Continued)

*Primary Examiner*—Bryan Bui
(74) *Attorney, Agent, or Firm*—Spencer K. Warnick; Hoffman, Warnick & D'Alessandro LLC

(57) ABSTRACT

A system, method and program product for determining the in-place engineering properties such as density and moisture content of many varieties of engineering materials, are disclosed. The invention also includes a database, material model and sensor model for use with the above-described aspects. In one embodiment, the invention determines a compaction indication of the material based on an effect of impedance characteristics of the material on an electrical field, and corrects the compaction indication for at least one of a sensor depth-sensitivity inaccuracy and a compaction process inaccuracy. The compaction indication is determined based on a material model, and the corrections are based on mathematical and empirical models of the compaction process and the sensor.

32 Claims, 8 Drawing Sheets

U.S. PATENT DOCUMENTS

| | | |
|---|---|---|
| 4,766,369 A | 8/1988 | Weinstein |
| 4,817,021 A | 3/1989 | Sowerby et al. |
| 4,933,853 A | 6/1990 | Musil et al. |
| 4,972,154 A | 11/1990 | Bechtel et al. |
| 5,051,026 A | 9/1991 | Sovik |
| 5,088,854 A | 2/1992 | Sovik |
| 5,134,380 A | 7/1992 | Jonas |
| 5,138,268 A | 8/1992 | Mulkey et al. |
| 5,210,500 A | 5/1993 | Pingel et al. |
| 5,213,442 A | 5/1993 | Sovik |
| 5,223,796 A | 6/1993 | Waldman et al. |
| 5,309,110 A | 5/1994 | O'Neill et al. |
| 5,363,051 A | 11/1994 | Jenstrom et al. |
| 5,378,994 A | 1/1995 | Novak et al. |
| 5,398,547 A | 3/1995 | Gerardi et al. |
| 5,436,565 A | 7/1995 | Gammell |
| 5,484,226 A | 1/1996 | Emerson et al. |
| 5,521,515 A | 5/1996 | Campbell |
| 5,551,288 A | 9/1996 | Geraldi et al. |
| 5,602,486 A | 2/1997 | Novak |
| 5,900,736 A | 5/1999 | Sovik et al. |
| 6,215,317 B1 | 4/2001 | Siddiqui et al. |
| 6,414,497 B1 * | 7/2002 | Sovik et al. ......... 324/663 |
| 6,577,141 B2 | 6/2003 | Gandrud |
| 6,615,648 B1 | 9/2003 | Ferguson et al. |
| 6,803,771 B2 * | 10/2004 | Sovik et al. ......... 324/654 |
| 2004/0095154 A1 | 5/2004 | Lundstrom et al. |
| 2004/0201385 A1 | 10/2004 | Dmevich et al. |

OTHER PUBLICATIONS

"Effective Impedance Measurement Using Open/Short/Load Correction", Agilent Technologies, Application Note 346-3, pp. 1-11, dated Jun. 1998.

* cited by examiner

TYPICAL MEASUREMENT PROFILE OF PLANAR CAPACITANCE-BASED IMPEDANCE SENSOR

DENSITY - DEPTH RELATIONSHIP FOR TYPICAL SOIL COMPACTION PROCESS

MATERIAL ANALYSIS INCLUDING DENSITY AND MOISTURE CONTENT DETERMINATIONS

This application claims benefit of U.S. Provisional Application No. 60/574,680, filed May 26, 2004, which is incorporated by reference herein.

BACKGROUND OF THE INVENTION

1. Technical Field

The present invention relates generally to material analysis, and more particularly, to the field of impedance spectroscopy, and the determination of engineering properties of a material such as density and moisture content from the response to electromagnetic probing in a defined frequency spectrum.

2. Related Art

Determination of engineering properties of materials such as density and moisture content is oftentimes desired. The engineering properties desired vary depending on application. For purposes of this application, one example application is compacting of engineering materials such as asphalt concrete or soil, which may be used in paving, building foundations, or the like. In this application, the degree of compaction is regarded as critical to the long-term durability of such systems. Under-compaction will result in poor strength and eventual settling that can cause cracking. Over-compaction results in poor performance due to the limited ability to absorb loads or handle moisture absorption.

The Proctor test (ASTM D698 and ASTM D1557) is used in the laboratory to determine the optimum moisture content for compaction and the maximum achievable compaction for a given amount of compaction energy. Field material compaction to achieve best engineering properties is specified to be at least 95% of the applicable Proctor test. The Sand Cone Test (ASTM D1556) is a known field test that can measure material density directly, but conducting the test requires considerable time and operator skill to produce accurate results. This test also requires digging a hole in the material that must later be repaired.

Several indirect methods exist that attempt to relate a measurable property of the material, such as resistance to penetration, to the in-place compaction. Such devices are known to use nuclear methods, mechanical penetrometers (both manual and electronic), and electrical impedance methods to measure a property of the material that can be related to density. Unfortunately, conventional devices do not adequately measure moisture content in a material, which is a highly desirable parameter. In addition, many of the indirect devices suffer from a number of deficiencies such as requirements for special storage, handling, and training. These deficiencies may be the result of use of nuclear sources, long measurement times, operator and material interface induced inaccuracies, the need for penetrating probes that must be carefully installed, and/or the inability to provide accurate measurements over the range of materials typically encountered in engineering practice. For example, material type, gradation, moisture content, and conductivity are known to affect prior art devices.

The dielectric permittivity of a porous mixture undergoing a compaction process increases with increasing density. This results from the displacement of air (dielectric constant=1) by solid materials (dielectric constant=3–5) and water (dielectric constant=80) in any volume of the material. It is further known that the permittivity of composite dielectric materials includes three components: a real part and an imaginary part, the latter of which includes a conductivity part and a dielectric loss part. The real part of the permittivity is related to energy storage and is commonly referred to as the dielectric constant. It is known in the art that the real part of the permittivity at certain frequencies in the electromagnetic spectrum is related to the density of the material. The imaginary part of the permittivity is related to energy loss and includes, as noted above, a conductivity part and a dielectric loss part. The conductivity part is related to ohmic conduction due to free ions, and the dielectric loss part is due to polarization losses from molecular, atomic, and interfacial dipole effects. The presence and amount of the three permittivity components is a function of the chemical and geometrical constituency of the material.

A number of approaches exist to measure one or more of the permittivity components of a material in order to physically determine properties of the material, and in particular, density and/or moisture content. One approach is disclosed by Blackwell in U.S. Pat. No. 3,784,905. The device of Blackwell has many disadvantages. For example, in order to obtain a reading, the Blackwell device must be moved at extremely slow speeds across the material being tested and, accordingly, requires an extended time period to provide a determination. The Blackwell device, due to its excessive weight, also requires a large sled frame (contact area) to be dragged across the pavement surface. Another disadvantage is limited adjustability of the depth of measurement of the device caused by the given set of electrodes only being able to vary the depth of measurement by changing the height of the electrodes. In addition, this device measures only the real component of the asphalt permittivity at a single frequency. As a result, it is not possible to determine whether conductivity or moisture has affected the reading. Further, the frequency employed by the Blackwell device is in a range where surface polarization effects resulting from surface conductive water will make the reading inaccurate.

In another apparatus taught by Regimand, U.S. Pat. No. 4,766,319, a nuclear source is used to determine density of pavement material. While the nuclear approach is considered by many to be technically adequate, the device has a variety of practical drawbacks. For instance, the device requires a licensed operator and a radiation shield, e.g., a lead enclosure. Furthermore, the device is non-adjustable for area, time-consuming in use, and heavy. In addition, storage, use, and disposal are strictly regulated and pose users with significant logistical and monetary expense. Recent concerns for homeland security have resulted in initiatives to eliminate devices that could be used by terrorists.

Another approach is taught by Siddiqui, et al. in U.S. Pat. No. 6,215,317. This patent describes a method and apparatus that uses time domain reflectometry (TDR) to determine the dielectric permittivity of compacted material. A number of practical disadvantages exist with the Siddiqui device. First, the device requires a penetrating probe to be driven into the material. The act of driving a probe into the material causes the density to change in the vicinity of the probe, causing errors in measurement. Another disadvantage of this device is the need to accomplish a single point field Proctor test in order to separate the effect of material moisture on the dielectric response from that of the material density. This results in an overall time to make a measurement of 10–15 minutes. Such measurement results in significant additional time on the job site such as a city street on which traffic must be stopped while repairs are being made to, for example, buried utility company equipment. A third deficiency with the Siddiqui device is their use of non-insulated probes to make the measurement. For materials that may have high conductivity, such as engineering materials, significant attenuation and consequent loss in resolution and accuracy can result.

Another known approach operates by determination of complex permittivity, and is taught by Sovik et al. in U.S. Pat. No. 6,414,497, which is assigned to TransTech Systems, the assignee of the present invention. The Sovik device operates by transmitting electromagnetic energy at a single frequency into the material via an arrangement of electrodes of a sensor. The material being measured becomes the dielectric of a capacitor formed by the electrodes (sensor elements). By measurement of the total permittivity and suitable calculations, the dielectric constant of the material, and hence the density may be determined using a single variant linear regression: In addition, the loss tangent of the total impedance, calculated as the ratio of the imaginary part of the permittivity to the real part, is used by the Sovik device to indicate the presence of moisture on a top surface of the material that may affect the measurement. The Sovik device makes a first order correction for this moisture, but is incapable of determining the bulk moisture content in the material. Further this correction is susceptible to error caused by a variable and unknown conductivity in the surface water. Unfortunately, many materials used for engineering purposes, such as soil, typically contain 6–9% water by weight. Additionally, conductivity as high as 10 mS/cm may be present in the form of dissolved salts (such as NaCl) in these materials. The electromagnetic response of dielectric materials containing water is such that the effects of water, conductivity, and particle geometry and the effects of density on the dielectric response cannot be separated using measurements made at a single electromagnetic frequency. Additionally, the forward mathematical model suggested in Sovik to relate the impedance to the density is based upon a presumed form that can be described in terms of a passive electrical equivalent circuit. Unfortunately, for complex materials such as soil, no adequate theoretical models exist to explain the complex interaction between the soil surface, water, and dissolved ions.

Another device, invented by Dr. Max Hilhorst (PhD thesis, "Dielectric Characterization of Soil," 1998), measures complex impedance at a single frequency to determine the moisture content and conductivity of soil. Devices that practice the teachings of Dr. Hilhorst are primarily applied to the determination of the moisture content and conductivity of soil in an agricultural context. The operating frequency of 20 MHz is selected so measurements are not influenced by surface polarization effects. By making the further assumption that the soil density and type is constant (reasonable in an agricultural measurement context), an in situ calibration can be performed that permits determination of the moisture content and conductivity using only a single frequency. As with the Sovik device, the Hilhorst device cannot simultaneously determine material density, and moisture content independent of conductivity and material type and particle size/shape effects.

In addition to the above-described deficiencies, all of the above-described devices exhibit inaccuracies due to a number of other factors such as the sensor used and the compaction process used to compact the material.

Another application is disclosed in Siconolfi, U.S. Pat. No. 6,125,297, in which an apparatus is described that determines the total body water content of living tissue using impedance spectroscopy using an electrical model of the body tissue. The device measures the complex impedance spectrum. As in Hilhorst, however, only moisture content and conductivity are calculated. Mean density effects are removed from the measurement by calibration. The device is also inaccurate because it is affected by the physiological state of the subject and by individual compositional variations.

In view of the foregoing, there is a need in the art for a material analyzer system that can accurately measure engineering properties such as density and moisture content of all varieties of materials.

SUMMARY OF THE INVENTION

The present invention provides a system, method and program product for determining the in-place engineering properties such as density and moisture content of many varieties of engineering materials. The invention also includes a database, material model and sensor model for use with the above-described aspects. In one embodiment, the invention determines a compaction indication of the material based on an effect of impedance characteristics of the material on an electrical field, and corrects the compaction indication for at least one of a sensor depth-sensitivity inaccuracy and a compaction process inaccuracy. The compaction indication is determined based on a material model, and the corrections are based on mathematical and empirical models of the compaction process and the sensor. The present invention does not require penetration into the material being measured, does not require special skills, training, or licensing to operate, and is insensitive to moisture and conductivity of the material. The present invention extends the teachings of U.S. Pat. No. 6,414,497, which is hereby incorporated by reference for all purposes, to measure engineering properties of materials that contain conductive water. The invention may employ a plurality of frequencies in conjunction with data processing to separate the effects of density, material type, moisture content, and ionic conductivity.

A first aspect of the invention is directed to a material analyzer system comprising: a sensor; and an analyzer unit including: an electronic circuit operatively coupled to the sensor for generating an electrical field from the sensor proximate the material; and a data analyzer, operatively coupled to the electronic circuit, that determines a compaction indication of the material based on an effect of impedance characteristics of the material on the electrical field, wherein the data analyzer corrects the compaction indication for at least one of a sensor depth-sensitivity inaccuracy and a compaction process related inaccuracy in one of a first mode and a second mode.

A second aspect of the invention is directed to A method for determining a compaction of a material, the method comprising the steps of: measuring an impedance of the material using a sensor; determining a compaction indication of the material based on the impedance; and correcting the compaction indication with at least one of a sensor depth-sensitivity correction and a compaction process correction.

A third aspect of the invention is directed to a computer program product comprising a computer useable medium having computer readable program code embodied therein for determining a compaction indication of a material, the program product comprising: program code configured to measure an impedance of the material based on a reading by a sensor; and program code configured to determine a compaction indication of the material based on the impedance, wherein the compaction indication is corrected using at least one of a sensor depth-sensitivity correction and a compaction process correction.

A fourth aspect of the invention is directed to a database for use with a material analyzer system that determines an engineering property of the material based on an impedance reading of the material, the database comprising at least one of: a sensor model for determining a sensor depth-sensitivity correction for the engineering property; and a compaction process model for determining a compaction process correction for the engineering property.

A fifth aspect of the invention is directed to a material model for use with a material analyzer system, the material model comprising: an empirical model for converting a complex impedance value of the material to an engineering property of the material, the empirical model implemented using a non-linear multiple variable-parameter estimator, wherein model parameters used by the estimator are based on known samples of the material.

A sixth aspect of the invention is directed to a sensor model for use with a material analyzer system, the sensor model comprising: an incremental contribution for a particular sensor at each increment of a lift depth.

A seventh aspect of the invention is directed to a material analyzer system comprising: a sensor; and an analyzer unit including: an electronic circuit operatively coupled to the sensor for generating an electrical field from the sensor proximate the material; and a data analyzer, operatively coupled to the electronic circuit, that determines a property of the material by implementing a material model capable of determining the property based on an effect of impedance characteristics of the material on the electrical field, wherein the material model implements a non-linear multiple variable-parameter estimator.

The foregoing and other features of the invention will be apparent from the following more particular description of embodiments of the invention.

BRIEF DESCRIPTION OF THE DRAWINGS

The embodiments of this invention will be described in detail, with reference to the following figures, wherein like designations denote like elements, and wherein.

DETAILED DESCRIPTION

For purposes of organization only, the description includes the following headers: I. Material Analyzer System Overview, II. Analyzer Unit Overview, III. Sensor Overview, IV. Electronic Circuit: Sensor and Measurement Circuits, V. Implementation of Models to Attain Compaction Indication in Form of an Absolute Density, VI. Operational Methodology, and VII. Conclusion.

I. Material Analyzer System Overview

The present invention determines one or more engineering properties of a material by measurement of electrical impedance thereof. One particular engineering property is a compaction indication as represented by a density of the material or a level of possible compaction. As used herein, "material" should be interpreted broadly to include all varieties of dielectric materials, e.g., asphalt, concrete, soil, ceramics, bituminous material, or other forms of in-place material such as biological tissue, crops (e.g., tobacco), foodstuffs (e.g., cereal), etc. The preferred embodiments may be described in conjunction with the measurement of compacted soil and, in one example, a utility cut/repair operation in which soil is compacted in a number of lifts. The particular application and material described herein, however, is not intended to be limiting. Other applications of the invention and materials will be apparent to those skilled in the art.

Figure 1:
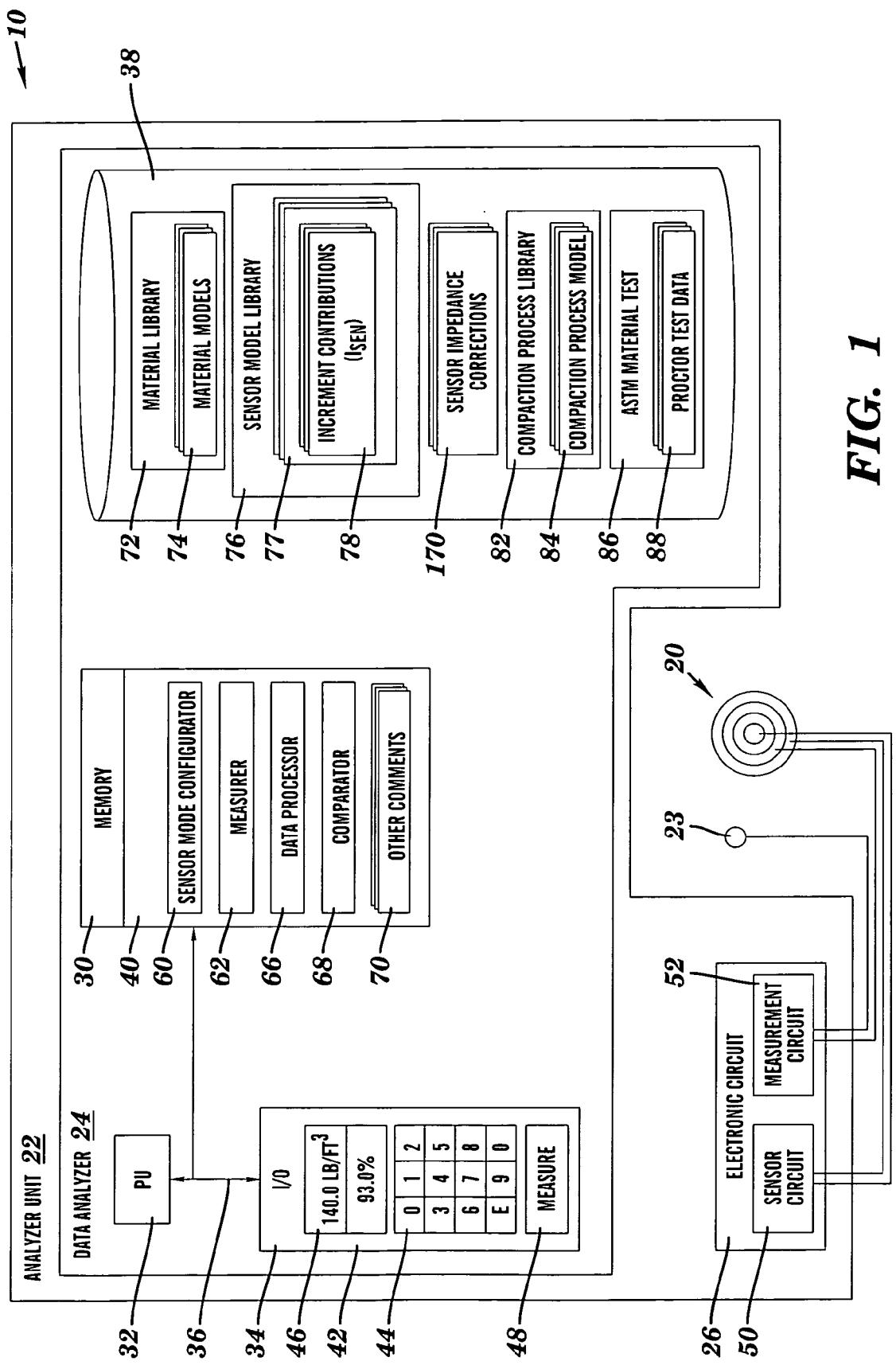
FIG. 1 shows a block diagram of a material analyzer system.

With reference to the accompanying drawings, FIG. 1 is a block diagram of a material analyzer system 10 in accordance with the invention. Material analyzer system 10 includes a sensor 20 and an analyzer unit 22. A temperature sensor 23 may also be provided for determining the temperature of a material under test.

II. Analyzer Unit Overview

With continuing reference to FIG. 1, analyzer unit 22 includes a data analyzer 24 and an electronic circuit 26 (described below). Data analyzer 24 includes a memory 30, a processing unit (PU) 32, input/output devices (I/O) 34 and a bus 36. One or more databases 38 may also be provided for storage of data relative to processing tasks, as will be described below. Memory 30 includes a program product 40 that, when executed by PU 32, comprises various functional capabilities described in further detail below. Memory 30 (and database(s) 38) may comprise any known type of data storage system and/or transmission media, including magnetic media, optical media, random access memory (RAM), read only memory (ROM), a data object, etc. Moreover, memory 30 (and database(s) 38) may reside at a single physical location comprising one or more types of data storage, or be distributed across a plurality of physical systems. PU 32 may likewise comprise a single processing unit, or a plurality of processing units distributed across one or more locations.

I/O 34 provides an operator interface(s) 42 including at least a numeric keypad 44 for entry of job site parameters and other information, and a display 46 to communicate measurement results to the operator. I/O 34 may also include circuitry to connect material analyzer system 10 to external devices such as other computers or printers or the like. Accordingly, I/O 34 may include any now known or later developed type of input/output device including a network system, modem, keyboard, mouse, scanner, voice recognition system, global positioning system (GPS), wireless Ethernet, CRT, printer, disc drives, etc. Additional components, such as cache memory, communication systems, system software, etc., may also be incorporated into material analyzer system 10.

Electronic circuit 26 includes a sensor circuit 50 and a measurement circuit 52. Sensor circuit 50 is an electronic circuit that: 1) applies an electric potential or current to sensor 20 to generate, or transmit, an electrical field; and 2) provides an active guard circuit to minimize unwanted interference from the surroundings and reduce or eliminate the effects on measurements of stray capacitances in the sensor. Measurement circuit 52 is an electronic circuit that receives the electrical potential or current from sensor 20, and converts the electrical signal into a useable medium. Further details of circuits 50, 52 will be described below Returning to data analyzer 24, program product 40 includes a sensor/mode configurator 60, a measurer 62, a data processor 66, a comparator 68 and other components 70. Other components 70 may include any other program code not expressly described herein, but necessary for operation of data analyzer 24. Each of the above-identified program product components will be explained in more detail below.

In one embodiment, one database 38 that is provided is a material library 72 that includes a number of material models 74. A "material model" 74 may include an empirical model (e.g., in form of an artificial neural network) for converting an impedance reading along with temperature and material type to one or more engineering properties such as moisture content, density, conductivity, etc., as will be described in more detail below. Another database 38 may include a sensor model library 76. Each "sensor model" 77 includes a finite element model including at least one set of increment contributions ($I_{sen}$) 78 for a particular sensor 20 and specified lift thickness (t). Each increment contribution indicates the particular sensor's sensitivity at an increment of the lift depth. That is, a percentage of the reading that the increment contributes to the overall reading. Another database 38 includes a compaction process model library 82. Each "compaction process model" 84 includes data suitable for determining of a relative volumetric density profile of a compacted lift of soil from operator entered job parameters. The purpose of the above-identified databases 38 and related data will be described below. Another database 38 may include standardized material classifications 86 such as an ASTM classification, and Proctor test data 88 for one or more of those materials identified by the ASTM material type.

It should be recognized that the above-described databases may be joined to form a unified database, or compartmentalized other than as shown.

III. Sensor Overview

Figure 2B:
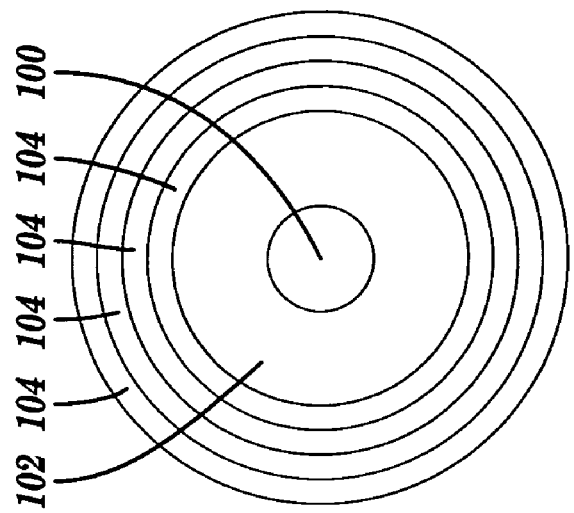
FIG. 2B shows a plan view of the sensor.
Figure 2A:
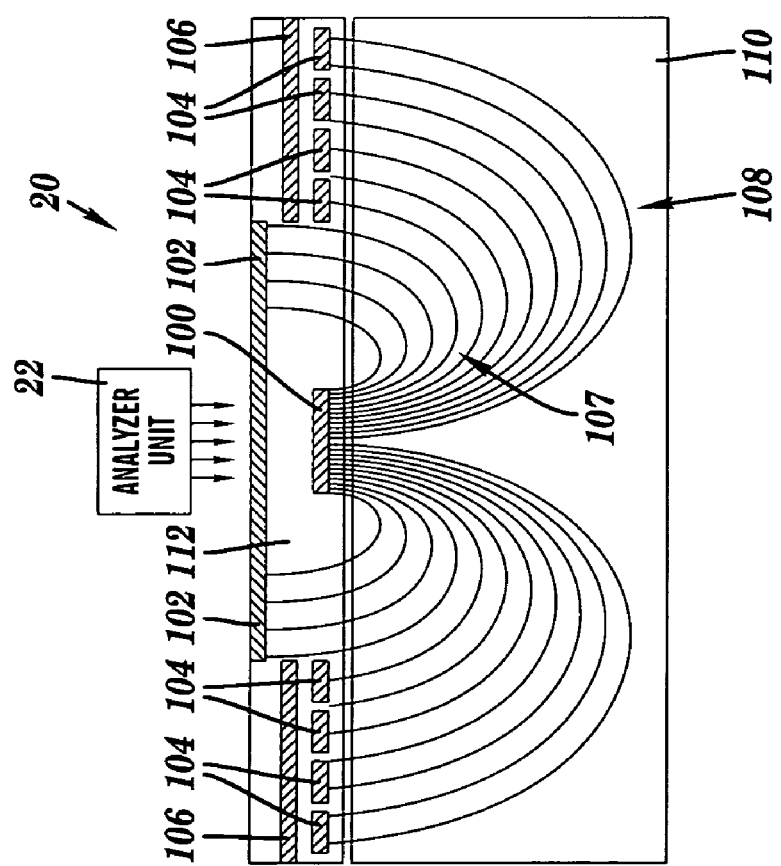
FIG. 2A shows a cross-sectional view of a sensor showing the electrical field penetration into the material.

Referring to FIGS. 2A and 2B, one embodiment of a sensor 20 is shown in greater detail. Sensor 20 preferably includes an active inner (transmit) element 100, an intermediate ground element 102 then one or more sense elements 104. Sensor 20 may also include a guard element 106. As shown in FIG. 2A, electrical field components 107 and 108 are created in a material 110 by applying an electric signal (from sensor circuit 50 shown in FIG. 1) to inner element 100. Electrical field 107 is transmitted from inner element 100 through material 110 to ground plane 102. Electrical field 108 is transmitted from inner element 100 through material 110 to sense element(s) 104. An advantageous function of the ground plane and the generation of electric field 107 is to direct electric field 108 to deeper portions of material 110 than would occur without the ground plane. This provides two advantages: first, a reduced sensitivity to imperfections on the surface of material 110, and second, a deeper penetration of field 108 and hence, a deeper measurement depth. Sensor 20 may be in contact with material 110 during use or separated from the material by a small air gap. The signal received by sense element(s) 104 is altered by the impedance characteristics of material 110. Sense element(s) 104 may be divided into a plurality of concentric annular elements for the purpose of controlling the depth of penetration of electrical field 108 into material 110. Guard element 106 is driven by an electrical potential substantially equal to that present on sense element(s) 104, and substantially reduces interaction of electrical field 108 with analyzer unit 22 and other external sources of electromagnetic interaction. Each of elements 100, 102, 104, 106 may be constructed of any good conducting material, but are preferably made of copper. Elements are held together and insulated from each other and from the material 110 by a non-conductive material 112 such as an epoxy or epoxy glass matrix.

The shape, size, and location of elements in a sensor 20 can be adjusted to accommodate different materials and measurement requirements. The specific configuration and geometry of the elements determines: 1) the minimum depth of measurement, 2) the maximum depth of measurement, and 3) sensitivity to stray capacitances within the apparatus. In one embodiment, each sensor 20 includes at least one corresponding sensor model 77 in sensor library 76 (FIG. 1).

IV. Electronic Circuit: Sensor and Measurement Circuits

Figure 3:
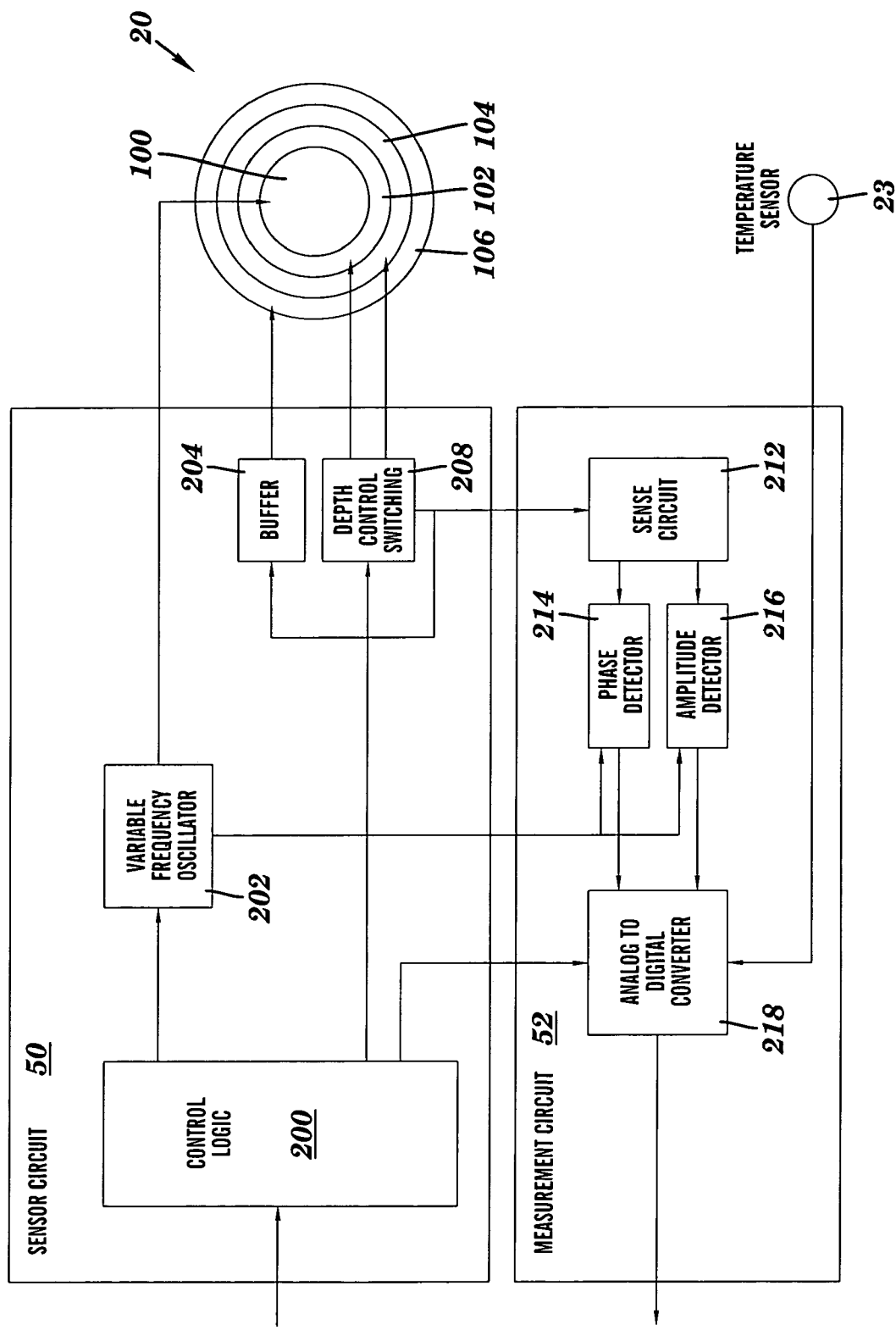
FIG. 3 shows a block diagram of a sensor circuit and a measurement circuit.

Turning to FIG. 3, details of sensor 50 and measurement 52 circuits will now be described. While preferred embodiments of these circuits will be described, it should be recognized that circuits 50, 52 may take a variety of forms. The invention, therefore, should not be limited to any particular circuit configuration other than as denoted in the attached claims.

Sensor circuit 50 includes control logic 200, a variable frequency oscillator 202, a buffer amplifier 204, and a depth control switch 208. Measurement circuit 52 includes a sense circuit 212, a phase detector 214, an amplitude detector 216 and an analog-to-digital (AD) converter 218.

In the illustrative circuits shown in FIG. 3, variable frequency oscillator (VFO) 202 is a constant amplitude low distortion sine wave generator. VFO 202 may produce a constant voltage or constant current according to the requirements of the application. A frequency of VFO 202 is set by control logic 200 under control of program product 40 (FIG. 1) executing in analyzer unit 22. A frequency range is preferably from 10 KHz to 30 MHz and is specific to material 110 (FIG. 2A). An output of VFO 202 is connected to inner transmit element 100 of sensor 20.

As previously stated with regard to FIGS. 2A and 2B, an electrical field(s) is induced into a material under test. A depth control switch 208 is used to interconnect/disconnect sense element(s) 104 so as to control a depth of penetration of the electrical field(s) into the material, as shown in FIG. 2A. The specific configuration of sensing element(s) 104 to produce a desired penetration depth is determined using finite element analysis techniques known in the art. In one embodiment, different arrangements of sensing element(s) 104 may be tested versus differing material, lift depth, and other characteristics, to determine depth penetration for the arrangements. Depth control switch 208 can be implemented using, for example, solid state switches or relays to control arrangements of sensing element(s) 104.

Sense element(s) 104 are connected to sense circuit 212 via depth control switch 208. Guard element 106 is driven by buffer 204 to maintain the electric potential equal to the potential on sense element(s) 104. Sense circuit 212 may include an electrical network, such as a fixed resistor, across which a potential is developed that is related to the impedance characteristics of the material. The magnitude and phase (relative to the VFO potential) of the potential developed by sense circuit 212 is measured by amplitude detector 216 and phase detector 214, respectively. The analog outputs of amplitude detector 216 and phase detector 214 are converted into digital form by AD converter 218 and supplied to program product 40 (FIG. 1) for processing. An output of temperature sensor 23 is also connected to AD converter 218 for supply to program product 40.

V. Implementation of Models to Attain Compaction Indication in Form of an Absolute Density The invention addresses, inter alia, inaccuracies of raw measured data used to determine engineering properties of a material such as a compaction level in the form of a density. Inaccuracies may be caused by, inter alia, the following issues: 1) the compaction process used, 2) the chemical and geometric composition of the material, 3) the non-uniform volumetric measurement (VM) profile of a sensor, and 4) errors resulting from imperfections in the sensor and electronic circuits. In order to remove inaccuracies caused by these issues, the invention implements four mathematical or empirical models. These models include, as shown in FIG. 1: a material model 74, a sensor model 77, a compaction process model 84 and sensor impedance corrections 170. In addition, the invention measures over a set of frequencies $f_l$ to $f_n$ such that improved corrections can be implemented. The appropriate set of frequencies is assigned based on the material characteristics. Accordingly, a frequency set may be included as part of a material model 74. This section will describe the present invention's implementation of the models to remove inaccuracies in a compaction indication in the form of an absolute density based on the above issues.

A. Raw Measurement Data and Initial Data Processing

Returning to FIG. 1, raw measurement data is obtained by sensor 20 and processed by program product 40 of data analyzer 24 of analyzer unit 22. "Raw measurement data" includes a material temperature T and a complex impedance at each one of a plurality of measuring frequencies $f_l$ to $f_n$. Raw measurement data includes information related to the impedance of the material as well as, inter alia, contributions from sensor 20 and associated wiring and components.

As an initial data processing step, "corrected measurement data" in terms of material impedance for each frequency is generated by isolating values from the other contributions to the raw measurement data by a process known in the art as "open/short/load compensation," as described in Agilent Corp. Application Note 346-3, which is hereby incorporated by reference for all purposes. Open/short/load compensation uses a model of the circuit to be compensated combined with impedance data taken under known conditions using standard impedances to estimate the values for errors introduced by stray circuit impedances. The result of this initial compensation is corrected measurement data in the form of a set of complex impedance values, one for each frequency of testing. This set can be represented mathematically as: $\{R_i, jX_i, f_i\}$, where $R_i$ is the real part of the complex impedance, and $X_i$ is the imaginary part of the complex impedance and $f_i$ is frequency of operation, and i is an integer.

In one embodiment, the above-described open/short/load compensation can be carried out for a variety of sensors and related wiring and equipment, and stored as a sensor impedance correction 170 (FIG. 1) in sensor library 72. A sensor impedance correction 170 then may be applied to the raw measurement data to isolate the required data from the other contributions to the raw measurement data.

B. Encoded Data

The permittivity (i.e., dielectric constant) of the material can be represented in complex form as:

$$\epsilon_r = \epsilon'_r - j\epsilon''_r,$$

where $\epsilon'_r$ is the real part of the permittivity, and $\epsilon''_r$ is the imaginary part of the permittivity. The real part $\epsilon'_r$ reflects the energy storage or capacitive part of the permittivity, and includes the density information. The real part $\epsilon'_r$ value is influenced, however, by material type, conductivity and moisture content. The imaginary part $\epsilon''_r$ is related to energy loss in the medium and can be expressed as:

$$\varepsilon''_r = \varepsilon''_d - \frac{\sigma_{DC}}{2\pi f \varepsilon_0},$$

where $\epsilon''_d$ is loss due to dielectric relaxations, $\sigma_{DC}$ is loss due to ohmic conductivity from dissolved ions in the water, f is frequency of operation and $\epsilon_0$ (epsilon zero) is the permittivity of free space. Ohmic conductivity $\sigma_{DC}$ is independent of frequency and is related to the ionic content in the water in the material. The losses due to dielectric relaxations $\epsilon''_d$ occur at frequencies that are dependent on the specific mechanism of the relaxation. Relaxations can be due to orientational polarization (due to dipole orientation), electronic polarization (due to electron cloud or molecule distortion), or interfacial interaction polarization between the water, dissolved ions and solid particles.

In terms of interfacial interactions, three major interfacial polarization effects have been identified: bound water polarization, Maxwell-Wagner effect polarization, and double layer polarization. "Maxwell-Wagner effect polarization" (hereinafter "M-W effect") is a macroscopic phenomenon that depends on the differences in dielectric properties of material constituents, e.g., rocks, oil, air, etc., and is a result of the distribution of conducting and non-conducting areas in the material matrix. The frequency range of the M-W resonance is material dependent and for soil, for example, is in the range of 300 KHz to 5 MHz. The frequencies of the M-W effect resonances and the spectral response just below and above the resonance are also influenced in a unique way by material moisture and conductivity. For material that is sand based, such as soil suitable for engineering use, the most important interfacial polarization effect is the M-W effect.

In the current invention, some of the frequencies used to generate a material model, as will be described below, are selected to permit determination of features that are related to the M-W resonance. Other frequencies are chosen to determine the permittivity in a frequency region where the polarization effects are not present, such as 10–50 MHz for example. The M-W resonance information is used in generating a material model to correct the measured real part of the permittivity for moisture content, conductivity, and soil type effects.

C. Material Model

Based on the above corrected measurement data, at least one engineering property output including, for example, an actual but raw (uncorrected) density $D_{raw}$ and actual moisture content $w_{raw}$, may be developed from the complex impedance values using a material model 74 (FIG. 1) of the material. It should be recognized that other engineering properties may also be outputted such as conductivity. Each material model 74 includes an empirical model for a given material for converting corrected measurement data and temperature to, for example, an actual density $D_{raw}$ and an actual moisture content $w_{raw}$. A material model 74 is selected based on material type. Inputs to material model 74 include the above-described corrected measurement data along with temperature. The corrected measurement data may be further processed to extract "features" that are also input to the material model 74 to produce an engineering property output. For the current example of soil, no theoretical models exist that adequately explain the complex relationship between the soil surface, the water, and the dissolved ions. In such cases, a model must be chosen that requires no a-priori knowledge of the functional relationship between the desired engineering properties and the input. Further the model must be capable of learning the required relationship by a process known as "supervised learning," wherein the model is presented actual or simulated measurement data along with independently measured values of the desired engineering properties.

In one embodiment, a material model 74 is implemented using a non-linear multiple variable-parameter estimator, which is trained to establish a number of model parameters that are particular to a material. The model parameters used by the estimator are estabilished based on known samples of the material. In one example, material model 74 is implemented using an artificial neural network (ANN) trained in the laboratory using data from samples that span the expected range of all engineering properties that are expected to influence the calibrated complex impedance. Such properties may include, for example, moisture content, density, temperature, conductivity and material type (including composition details such as gradation). The model is built over a set of frequencies $F_{set}$ that are preferably re-used when the material in issue is the same as the material model's. It is emphasized, however, that model parameters generated by the material model may vary depending on the material. For example, model parameters used relative to biological samples may not be the same as those used for foodstuffs, soils, etc. Model parameters are analogous to "layer weights" as that term is used relative to ANNs.

An illustrative implementation of a material model employs a back propagation artificial neural network to learn and implement the transfer function that converts the corrected impedance data into, for example, the uncorrected estimates of the density $D_{raw}$ and moisture content $w_{raw}$. Artificial neural networks (ANNs) have been successfully applied to non-linear function synthesis problems. It has been shown theoretically that a three-layer network can solve an arbitrary order transfer function between a set of inputs and outputs. A significant advantage of the neural network approach in functional synthesis problems is the ability of the ANN to discover complex and non-linear functional relationships between some physical phenomenon (e.g., soil density and moisture content) and a set of variables that contain information about the phenomenon. In this sense, an ANN is a programmable transfer function that 'learns' its parameters from data presented to it, rather than being programmed in advance. Neural networks have been shown to be effective in many types of problems in which sufficient a priori data is available to train the network. Such 'training data' must encompass all the features that the network will be required to recognize. When properly trained, neural networks show significant capacity to generalize, i.e., recognize generalized features and reject uncorrelated noise. For the case of soil measurement, the corrected impedance data contains "features" related to moisture content, conductivity, material type, and density, which are used by the ANN. These features, however, are highly encoded in the corrected measurement data, as described in the above section. For example, the imaginary part of the permittivity at frequencies above approximately 20 MHz contains the information proportional to density. In addition, the real part contains information about the conductivity and moisture content.

While it is not possible with simple analysis to discover the precise relationships between engineering properties, "features" that are influenced by variations in the properties can be derived from the corrected impedance data for use as inputs to the material model 74. The features are material dependent and are derived based upon analysis of raw impedance spectra from a large number of samples in the region of the M-W resonance in which engineering properties such as density, conductivity, and moisture content were varied in a known way. In one embodiment, the derived features applied to material model 74 include at least one of: frequency of a Maxwell-Wagner resonance, a slope at the Maxwell-Wagner resonance, a magnitude and a slope of a real part of a permittivity in a frequency region below the Maxwell-Wagner resonance, a magnitude and a slope of the real part of the permittivity in a frequency region above the Maxwell-Wagner resonance, and an imaginary part of the permittivity at a frequency above the Maxwell-Wagner resonance.

It should be recognized that material model 74 need not be implemented using an artificial neural network (ANN), and that other forms of a non-linear multiple variable-parameter estimator may be employed.

D. Compaction Process Model

In a typical utility cut/repair operation, an opening may be made, for example, having an approximately cubical shape having sides 3–6 feet in extent and a depth of 3–6 feet. A repair is typically accomplished by placing and compacting individual layers (hereinafter referred to as "lifts") of material in 6–12 inch depths in the opening. Compaction may be accomplished, for example, using handheld vibratory plate compactors. To minimize the total amount of time to accomplish the repair, there is a desire to use the largest lift possible. With larger lifts, however, comes greater variation in the finished volumetric density profile and, accordingly, greater variation in density.

Figure 4:
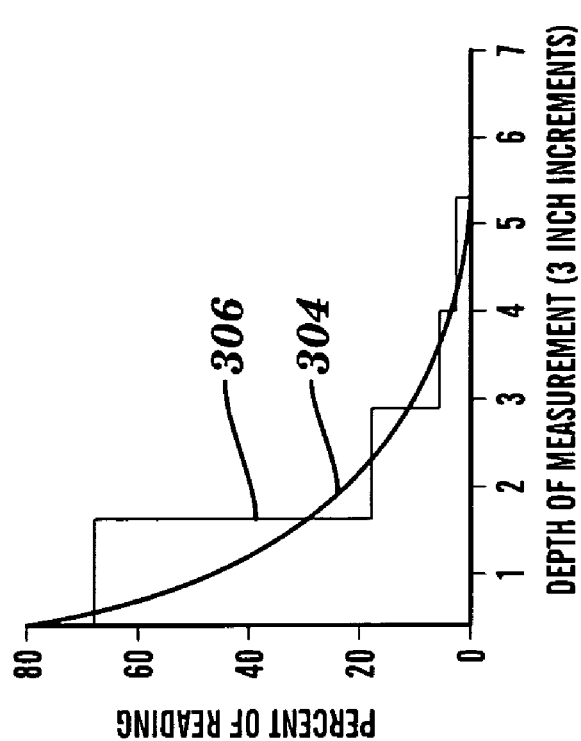
FIG. 4 shows a graph showing a compaction profile of a typical street cut repair.

Each compaction process model 84 (FIG. 1) includes a theoretical or empirical model for computing the relative volumetric density (VM) profile for a compaction process. FIG. 4 illustrates a two-dimensional version of a VM profile. Based on the VM profile, a mean relative density $D_m$ can be established for a lift, as will be described below.

A compaction process model 84 may be generated similarly to material model 74. The compaction process model may be implemented using techniques such as finite element modeling to relate known process parameters to the process output. Parameters may include, for example, opening size, material to be compacted, structural/mechanical condition of material (average particle size, moisture, etc.), type of compactor (e.g., roller, plate, vibration-capable, size, etc.), a compactive energy profile of a compactor, process parameters (e.g., outside-to-inside spiral path) or boundary conditions associated with the opening (e.g., elastic modulus). As will be described below, inputs by an operator of analyzer unit 22 allow for recall of an appropriate compaction process model.

Figure 5:
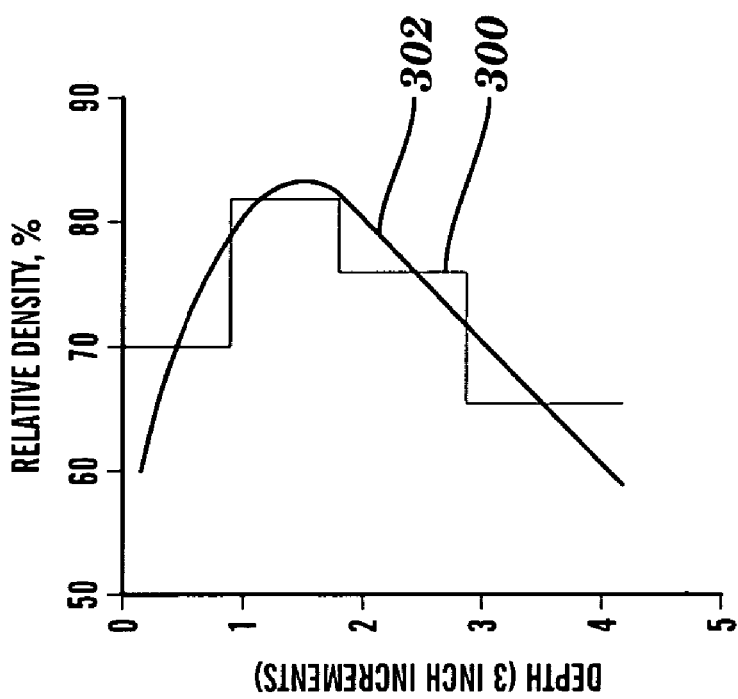
FIG. 5 shows a graph showing measurement depth versus percent of reading for a sensor.

FIGS. 4 and 5 will be used in the following discussion to describe the method by which the models are used to correct the raw density measurement $D_{raw}$ for compaction process inaccuracies that may be introduced by the particular sensor and compaction process used. In FIG. 4, a VM profile from a typical material compaction process of a twelve (12) inch depth lift is shown. The density profile plots depth in three (3) inch increments (1–4) versus relative density, i.e., a percentage of possible compaction. Increment 1 indicates density for 0–3 inches from the surface, increment 2 for 3–6 inches from the surface, increment 3 for 6–9 inches and increment 4 for 9–12 inches. Curve 302 represents an illustrative actual density profile, and a stepped curve 300 represents a linearized value for each increment. In particular, stepped curve 300 indicates the density in each three inch increment (1–4) of depth as a constant value equal to the mean of actual density profile curve 300 in the increment.

A relative mean density, $D_m$, for a lift can be defined as the sum of the actual density readings of each increment times the volume fraction of total depth of each increment. In the case of the FIG. 4 lift, the volume fraction for each increment is 0.25, i.e., 3 inches/12 inches. Assume, for example, the $D_{raw}$ for increment 1 is 115 pounds/ft³ (pcf), increment 2 is 120 pcf, increment 3 is 116 pcf, and increment 4 is 100 pcf. In this case, the relative mean density $D_m$ is 0.25*(115+120+116+100)=112.8 pounds/ft³ (pcf). As will be discussed below, however, each increment does not contribute equally to the measurement produced by a sensor. Accordingly, if the density profile is not taken into account, the sensor may not report an accurate relative mean density Dm.

E. Sensor Model

For an ideal sensor, each depth increment would contribute the same amount to the total reading. For example, an ideal sensor for the 12 inch lift, described above, would contribute 25% of the reading from each (3 inch) increment, i.e., $I_{ideal}$=[0.25, 0.25, 0.25, 0.25]. However, this is not possible in practice because electromagnetic sensors do not measure uniformly from the surface of a lift across a depth thereof. To illustrate, FIG. 5 plots a two-dimensional volumetric sensitivity (VP) profile for a typical sensor. The VP profile shown indicates a percentage of total reading as a function of depth increment contribution to the total reading. Curve 304 depicts an actual response, while stepped curve 306 provides a stepwise linearized version for use describing corrections. In particular, stepped curve 306 indicates the percent of reading in each three-inch increment (1–4) of depth as a constant value equal to the mean of actual response curve 306 in the increment.

As shown in FIG. 5, a larger percentage of a reading comes from material closest to a surface, e.g., increment 1 contributes to approximately 70% of the reading, increment 2 contributes 20%, increment 3 contributes 7%, and increment 4 contributes 3%. As noted above, each sensor model 77 (FIG. 1) includes a finite element model including at least one set of increment contributions ($I_{sen}$) 76 (not to be confused with the above-described sensor impedance correction 170) for a particular sensor 20 and a specified lift thickness (t). Each increment contribution ($I_{sen}$) indicates the particular sensor's sensitivity at an increment of the lift depth. That is, a percentage of the reading that the increment contributes to the overall reading. As with the above-described models, a sensor model may also be generated by a finite element model based on parameters such as sensor geometry, electromagnetic properties of sensor, materials to be sensed, and/or sensor material, etc.

Isolated measurement data compensated for non-uniformity of measurement, i.e., sensor depty-sensitivity inaccuracy, can be calculated by summing the multiples of those increment contributions by their actual density. Using the VS profile shown in FIG. 5, the actual increment contributions ($I_{sen}$) are 0.7, 0.2, 0.07, 0.03 for increments 1–4, respectively. Based on the above assumptions for $D_{raw}$, a measurement compensated for non-uniformity of measurement would give a density estimate:

$D$=(0.7*115)+(0.2*120)+(0.07*116)+(0.03*100)
 =115.6 pcf.

To illustrate the inaccuracies created, this value represents an error of 2.5% versus relative mean density $D_m$ calculated above (i.e., (115.6−112.8)/112.8). That is, a 2.5% error from not including the corrupting effects of the compaction process and sensor. Unfortunately, measurement accuracy of 1% is a target in order to assess compliance with the typical compaction specifications.

F. Correction Terms

In order to remove inaccuracies in an uncorrected density $D_{raw}$, a number of correction terms are derived and combined into a "correction factor" based on the above-described compaction process and sensor models.

One correction term is a compaction process correction that addresses errors based on the non-uniform density resulting from the compaction process. In one embodiment, the compaction process correction is implemented as a mean-variance correction term $D_{cor}$ that combines the effects of the VM profile (FIG. 4)(compaction process model) and the VS profile (FIG. 5)(sensor model) into a multiplier for each depth increment. The mean-variance correction term $D_{cor}$ represents a factor by which each increment's reading differs from the relative mean density $D_m$ for the entire lift of material. For the above-described example, mean-variance correction term $D_{cor}$ for increment 1=0.98 (i.e., 112.8/115), for increment 2=0.94 (i.e., 112.8/120), for increment 3=0.97 (i.e., 112.8/116) and for increment 4=1.13 (i.e., 112.8/100). That is, $D_{cor}$=[0.98, 0.94, 0.97, 1.13].

Another correction term is a sensor depth-sensitivity correction that addresses non-uniform contribution of each increment to the reading based on the sensor model. As noted above, an ideal sensor has equal contribution to the total reading from each depth increment. For the example shown in FIGS. 4 and 5, an ideal sensor would contribute 25% of the reading from each (3 inch) increment, i.e., $I_{ideal}$=[0.25, 0.25, 0.25, 0.25]. In one embodiment, a sensor depth-sensitivity correction addresses variances from the ideal increment contributions by providing each increment's contribution for a particular sensor and a specified lift thickness, as described above. For the example above, sensor depth-sensitivity correction term is $I_{sen}$=[0.7, 0.2, 0.07, 0.03]. This correction term set ($I_{sen}$) is stored for a particular sensor and a specified lift thickness (t) as part of sensor model 77 (FIG. 1).

G. Absolute Density

Based on the above correction terms, an absolute density $D_{true}$ can be calculated according to the following:

$D_{true}=D_{raw}/\text{Sum}(I_{sen}/D_{cor})$.

The term Sum ($I_{sen}/D_{cor}$) represents the "correction factor." Applying this formula to the above example, ($I_{sen}/D_{cor}$) would be for increment 1=0.714, increment 2=0.213, increment 3=0.072 and increment 4=0.029, which results in correction factor=1.028. Assuming a raw density $D_{raw}$ of, for example, 115.6, the absolute density $D_{true}$ would then be calculated as 112.8 pcf, as required.

VI. Operational Methodology

Referring to FIGS. 6A–D, a flow diagram of one embodiment of operational methodology for material analyzer system 10 is illustrated. The description that follows will reference FIGS. 6A–6D in conjunction with FIG. 1. As noted above, system 10 provides for three modes of operation of the apparatus:

Absolute Mode 1 uses a material model 74 from material library 72 to determine moisture content and a compaction indication in the form of an accurate absolute density $D_{acc}$. Absolute Mode 1 provides the highest accuracy but requires knowledge of the material, compaction equipment and procedure.

Absolute Mode 2 uses operator entered general data about the compaction equipment, compaction process and material type to determine an estimated moisture content $w_{raw}$ and a compaction indication in the form of an estimated absolute density $D_{est}$. Absolute Mode 2 accepts operator entry of a Proctor test data or will support an operator conducted field Proctor test and subsequent entry of the results to determine an approximate material model, rather than direct input of a known material model as in Absolute Mode 1. The approximated material model is based on the closest existing material in material model library 74 specified by the operator in the Proctor test field, e.g., ASTM number ($m_{id}$ as described below). Alternatively, it could be based on an inputted manual soil characterization, e.g., sandy, clay, etc. As noted above, a Proctor test is a test that determines the optimum moisture content ($w_{opt}$) for compaction and the maximum achievable density for a given amount of compactive effort. Estimated absolute density $D_{est}$ is calculated identically to absolute accurate density $D_{true}$ except that the material model used to determine raw density $D_{raw}$ is the approximated material model. Accordingly, absolute Mode 2 may produce reduced accuracy compared to Absolute Mode 1.

Relative Mode 3 is used when no information regarding the material or compaction equipment is available. As a result, no absolute density (estimated or accurate) or moisture content is determined. In contrast, a compaction indication in the form of relative level of compaction is provided to an operator. The relative level of compaction may include, for example, an indication when the maximum density achievable for the current conditions and equipment has been reached and/or a percentage of additional compaction achieved compared to a prior compaction pass.

Initially, it is noted that program product 40 (FIG. 1) components fulfill the corresponding generalized purposes: sensor/mode configurator 60 provides functioning relative to determining a mode of analyzer unit 22 and collecting related data for analyzer unit setup; measurer 62 provides functioning relative to actual measurements made by sensor 20; data processor 66 provides all data processing functioning including that related to implementing models 74, 77, 84, 170 and output determinations; and comparator 68 provides comparison functioning, where necessary. While the invention will be described relative to the above compartmentalization of functions, it should be recognized that the arrangement shown is meant to be illustrative and that other organization of functions is possible within the scope of the invention.

Figure 6A:
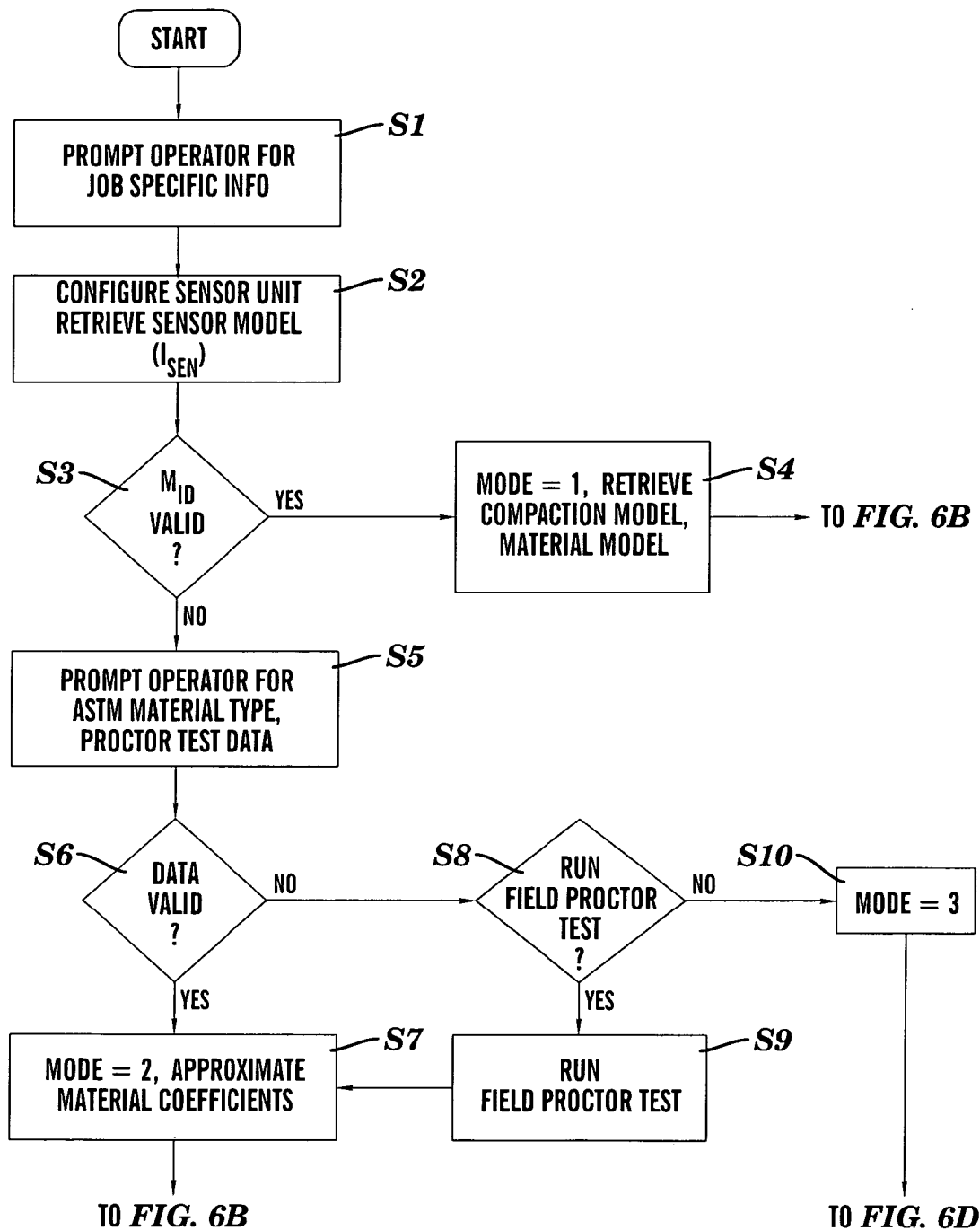
FIGS. 6A–D shows a flow diagram of an operational method of the material analyzer system of FIG. 1.

Referring to FIG. 6A, sensor 20 and mode configuration including initial data collection and instrument mode assignment steps are conducted by sensor/mode configurator 60. FIG. 6A logic begins at step S1 in which the operator is prompted for job specific information via I/O 34, e.g., as a graphical user interface (GUI). Such information may include, for example, job identification ($j_{id}$), cut size (length ($c_l$), width ($c_w$), depth ($c_d$)), a sensor identification ($s_{id}$), compactor identification ($c_{id}$), compaction process identification ($cp_{id}$), lift thickness (t), and material identification ($m_{id}$). A "job identification" ($j_{id}$) may be any alphanumeric or other representation for identifying a particular job. "Compactor identification" ($c_{id}$) may be any alphanumeric or other representation for identifying a particular type of compactor, e.g., vibrator, roller, types or models of each, etc. A "compaction process identification" ($cp_{id}$) may be any alphanumeric or other representation for identifying a compaction process. "Material identification" ($m_{id}$) may be any alphanumeric or other representation for identifying the material to be compacted. For example, material identification ($m_{id}$) may be an ASTM soil classification or a proprietary classification for a specific soil material from a specific source.

Next, in step S2, sensor 20 (FIG. 1) is configured by sensor/mode configurator 60 based on the specified lift thickness (t). In one embodiment, this step includes retrieval from storage, e.g., sensor library 76 (FIG. 1), of a sensor model 77 including an increment contribution ($I_{sen}$) 78 corresponding to sensor 20, i.e., sensor identification ($s_{id}$), and the specified lift thickness (t). In addition, a sensor impedance correction 170 may be retrieved.

At step S3, the entered material identification ($m_{id}$) is evaluated to determine if it is valid, i.e., whether the identification is a recognized material identification, by sensor/mode configurator 60. If $m_{id}$ is valid, then control proceeds to step S4 where an instrument mode is set =1 for Absolute Mode 1. In addition, a material model 74 (FIG. 1) and frequency set $F_{set}$ is retrieved from material library 72 (FIG. 1) based on the material identification $m_{id}$ and is initialized with the job specific information ($c_l$, $c_w$, $c_d$, $c_{id}$, $cp_{id}$, $s_{id}$, and t). As noted above, a "material model" is an empirical model for converting corrected measurement data into engineering properties such as moisture content, density and conductivity. Material model 74 may also include a set of measurement frequencies $F_{set}$ to be used for the material. In addition, a compaction model 84 may be retrieved at this step based on the inputted compactor identification ($c_{id}$) and/or compaction process identification ($cp_{id}$).

Subsequently, processing continues with step S100 in FIG. 6B, as will be described below. If, however, $m_{id}$ is not valid at step S3, then processing continues to step S5 at which the operator is prompted for an ASTM material (e.g., soil) type ($m_t$) and Proctor test data ($w_{opt}$, $g_{max}$). Next, at step S6, the data entered at step S5 is evaluated for validity. The data is valid if it properly indicates that the ASTM material type ($m_t$) is recognized and the Proctor data is available (entered). In one embodiment, this may entail determining whether the ASTM material type 86 is in a database, and whether the Proctor test data 88 for that material is also present.

If the data is valid, at step S7, the instrument mode is set=2 for Absolute Mode 2 and sensor/mode configurator 60 makes an approximation as to which material model is most appropriate for the material. The approximation may be made in a number of fashions. In one example, the approximation is made based on the Proctor data. In another example, the approximation may be made by selecting a material model for a material having the most similar characteristics, e.g., function (e.g., in the body: heart muscle, bone, skin, etc.; engineering material: aggregate size), size, chemical makeup, etc., as the material at issue. Once the approximation is completed, processing then continues with step S100 in FIG. 6B.

If the data is invalid at step S6 this indicates that the ASTM material type ($m_t$) is not recognized or the Proctor data is not available (not entered). In this case, at step S8, the operator is given the option to run a single point field Proctor test to supply the missing data. If the operator selects the field Proctor test option (i.e., YES at step S8) processing continues to step S9, where sensor/mode configurator 60 runs the test and related data is collected. Subsequently, processing proceeds to step S7, where the instrument mode is set=2 for Absolute Mode 2, and the above-described approximation of a material model is made. If the operator selects not to conduct a field Proctor test (i.e., NO at step S8), processing continues to step S11 where the instrument mode is set=3 for the Relative Mode. The job and material parameters that were not entered in the previous steps are set to default values and processing continues with step S300 in FIG. 6D. As an alternative embodiment, it may also be advantageous to run a field Proctor test at step S8 even if data is found valid at step S6.

Figure 6B:
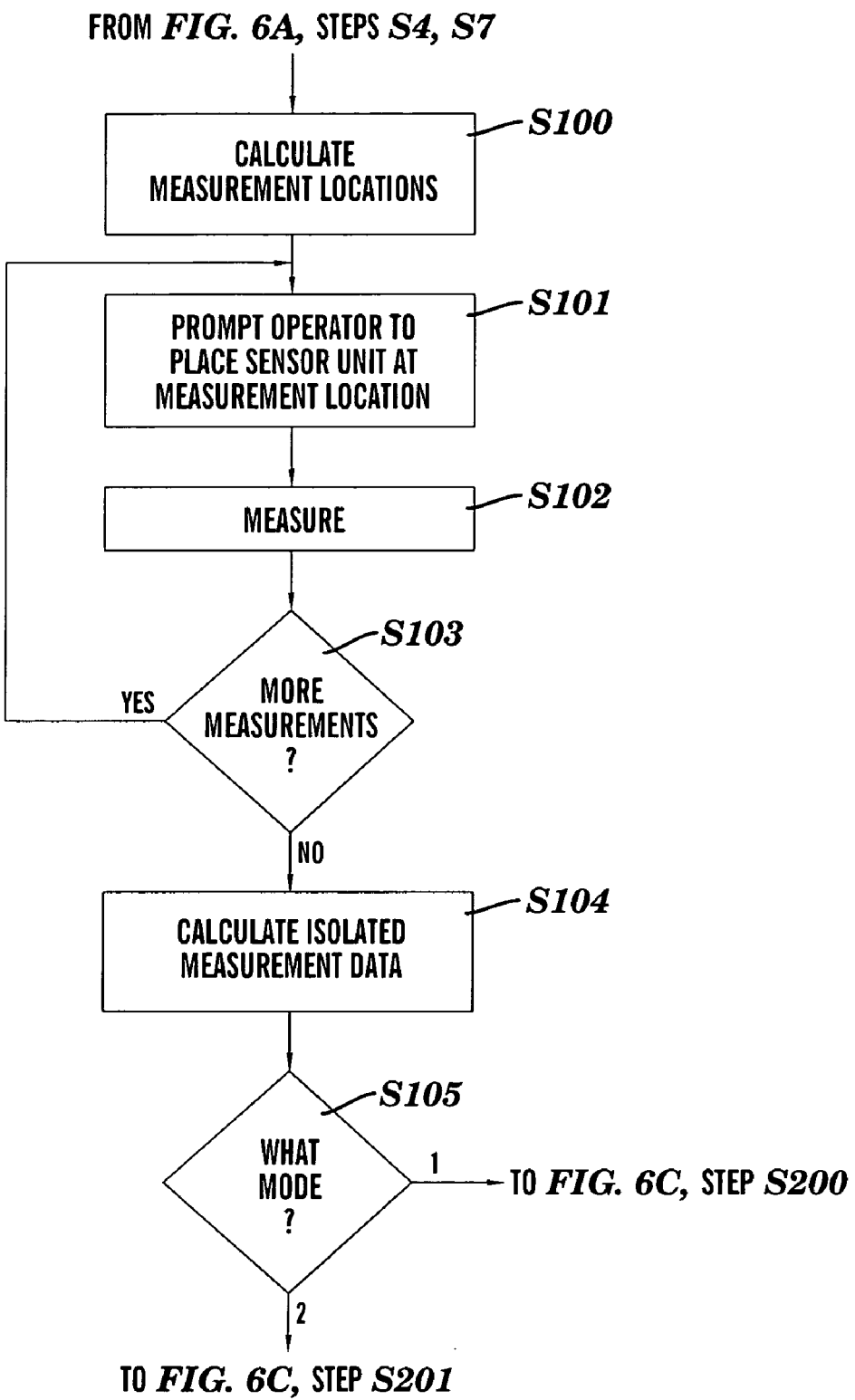

Referring to FIG. 6B, step S100 through S105 provide measurement data acquisition for the Absolute Modes 1 and 2 by measurer 62. That is, measurement data acquisition subsequent to either step S4 or step S7 in FIG. 6A. At step S100, specific measurement locations on the cut surface are calculated from the job specific information ($c_j$, $c_w$, $c_d$, $c_{id}$, $cp_{id}$, $s_{id}$, and t) and material model 74 by measurer 62 (FIG. 1). At step S101 the operator is prompted to place sensor 20 at the next measurement point. Actual prompting may occur in a number of fashions, for example, a flashing icon on a graphical depiction of the cut may be displayed on an instrument display 46 (FIG. 1). At step S102 a measurement is made by measurer 62, e.g., when the operator presses a "measure" key 48 of interface 42. In this step, measurer 62 activates sensor 50 and measurement 52 circuits to acquire the complex impedance data (magnitude and phase) for each frequency $f_1$ to $f_n$ in a set $F_{set}$ defined for the particular material under test, i.e., as part of a material model 74. If more measurements are to be taken, control reverts to step S101 per step S103. A number of measurements to be taken can be predetermined, for example, based on the size of a cut or other procedure.

Otherwise, processing continues to step S104 where corrected measurement data is calculated to remove sensor contributions via sensor impedance correction 170 or an actual open/short/load compensation correction by data processor 66, as described above. The result of this initial compensation is corrected measurement data in the form of a set of complex impedance values, one for each frequency of testing. This set can be represented mathematically as: $\{R_i, jX_i, f_i\}$, where $R_i$ is the real part of the complex impedance, and $X_i$ is the imaginary part of the complex impedance and $f_i$ is frequency of operation, and i is and integer. At step S105, a determination of the instrument mode is made by data processor 66. If in Absolute Mode 1, processing continues to step S200 in FIG. 6C; and if in Absolute Mode 2, processing continues to step S201 in FIG. 6C.

Figure 6C:
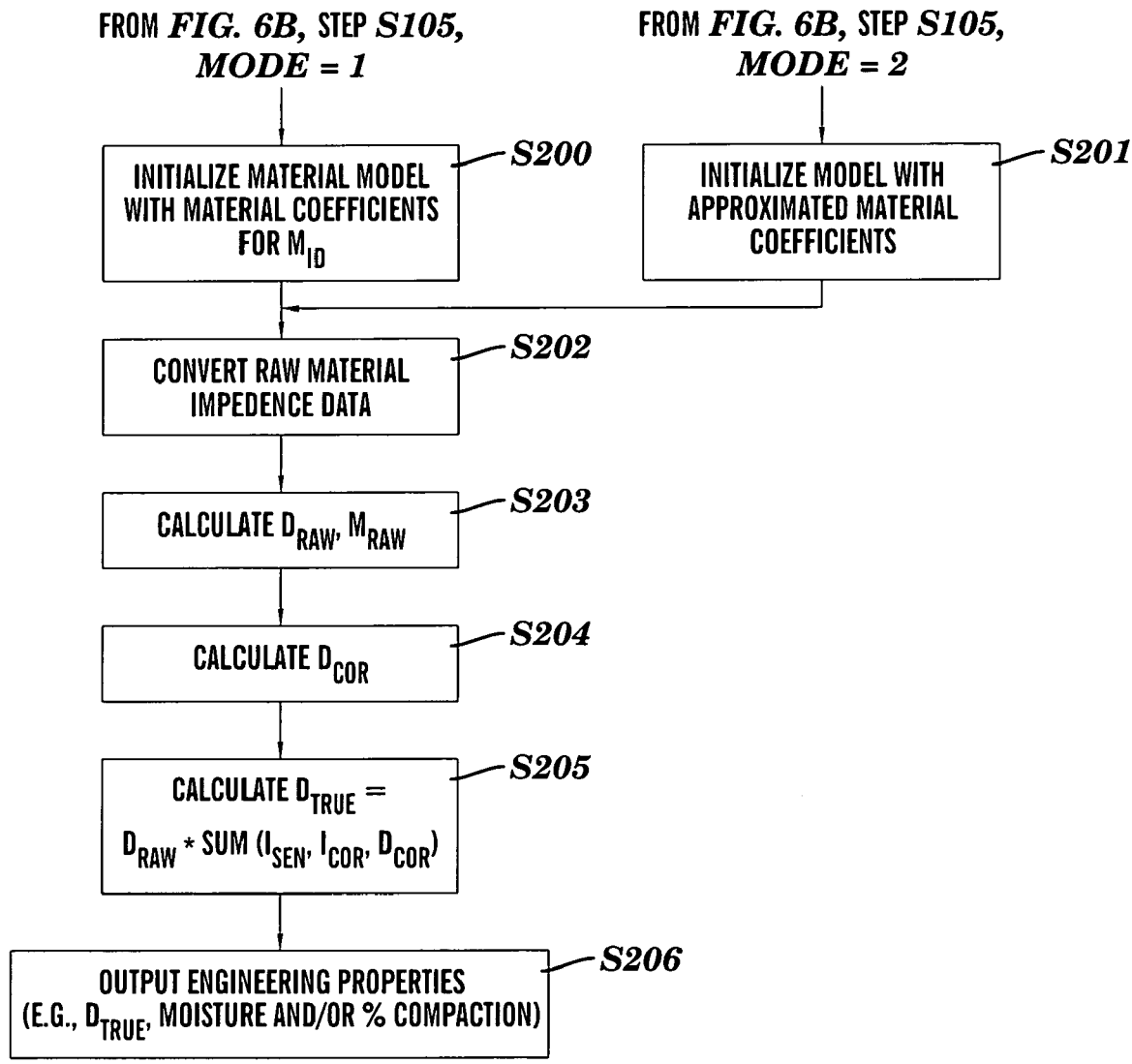

Turning to FIG. 6C, data processing relative to Absolute Modes 1 and 2 will now be described. At step S200, for Absolute Mode 1 (i.e., 1 at step S1105 of FIG. 6B), material model 74 is initialized with model parameters corresponding to $m_{id}$ by data processor 66. (FIG. 1). As described earlier, an exemplary implementation of a material model 74 implements a non-linear multiple variable-parameter estimator in the form of, for example, an artificial neural network (ANN) to learn and implement the transfer function that converts the corrected impedance data set into the uncorrected estimates of the density ($D_{raw}$) and moisture content ($w_{raw}$). Processing continues with step S202 after step S200, as will be described below.

Alternatively to step S200, for Absolute Mode 2 (i.e., 2 at step S1105 of FIG. 6B) processing begins with step S201 in FIG. 2C. Absolute Mode 2 differs from Absolute Mode 1 in that no specific data exists for the general material type specified. In this case, at step S201, data processor 66 (FIG. 1) initializes model parameters of the approximated material model as calculated at step S7 (FIG. 6A). Subsequently, processing continues with step S202.

Turning to step S202, processing continues by data processor 66 (FIG. 1) converting the corrected measurement data $\{R_i, jX_i, f_i\}$ into a new set of data wherein the components more closely match the features that the ANN will use to convert the isolated impedance data into $D_{raw}$ and $w_{raw}$. The features, as described above, may include: frequency of a Maxwell-Wagner resonance, a slope at the Maxwell-Wagner resonance, a magnitude and a slope of a real part of a permittivity in a frequency region below the Maxwell-Wagner resonance, a magnitude and a slope of the real part of the permittivity in a frequency region above the Maxwell-Wagner resonance, and an imaginary part of the permittivity at a frequency above the Maxwell-Wagner resonance. It should be recognized that the specific features used may vary; and the features listed above are not meant to be limiting. Additional processing, e.g., principle component analysis, may be applied to normalize the data and render features more easily discernible to the ANN.

Next, at step S203, data processor 66 (FIG. 1) computes the raw density ($D_{raw}$) and moisture content ($w_{raw}$) using the ANN and the incorporated model parameters thereof. Next, in step S204, compaction process correction ($D_{cor}$) is calculated by data processor 66 (FIG. 1) for the current job conditions from the compaction process model. At step S205, the absolute density ($D_{true}$) (estimated or accurate) is calculated by data processor 66 (FIG. 1) from $D_{true}=D_{raw}/\text{Sum}(I_{sen}/D_{cor})$, as previously described. Finally, at step S206, the absolute density, moisture content, and percent compaction are displayed on instrument display 46, e.g., 140 pcf and 5% (by weight), as shown in FIG. 1.

Figure 6D:
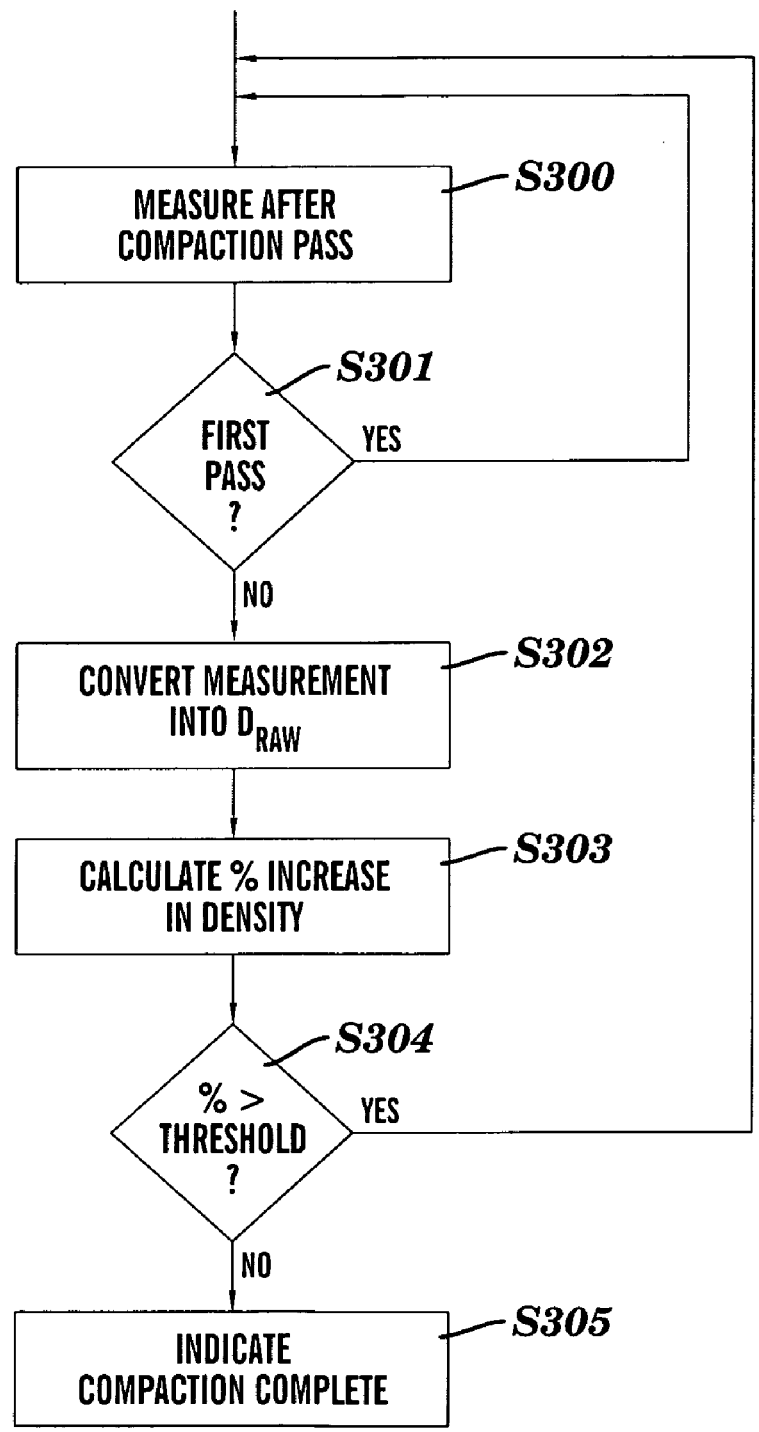

Referring to FIG. 6D, processing for Relative Mode 3 will now be described. In Relative Mode 3, the instrument is used between each compaction pass to ascertain when the material has been compacted to the highest value possible for the job conditions. That is, since no material specific calibration data is known, only a relative compaction value after each pass is made.

In a first step S300, the operator is prompted to take a measurement over the cut surface after a compaction pass by measurer 62 (FIG. 1). For typical engineering materials, the number of required compactor passes is from four to six. In this step, measurer 62 activates sensor 50 and measurement 52 circuits (FIG. 3) to acquire the complex impedance data (magnitude and phase) for each frequency $f_i$ to $f_n$ in a set defined for the particular material under test, i.e., as approximated. At step S301, a determination is made as to whether the current pass was the first pass by measurer 62 (FIG. 1). In one example, this determination can be made by prompting the operator to answer the query. If YES at step S301, processing returns to step S300 for another measurement. If NO at step S301, processing continues to step S302 where the measurement data is converted into $D_{raw}$ using nominal data for data processor 66 (FIG. 1). "Nominal data" may be established, for instance, by operator specification of the generic material type. In step S303, the percentage increase in density is calculated, for example, from an exponential curve fit of the available data by data processor 66 (FIG. 1). At step S304, comparator 68 (FIG. 1) compares the calculated percentage increase in density from the previous compactor pass with a predetermined threshold, e.g., 2%, which can be operator specified. If the increase in density is greater than the threshold, i.e., YES at step S304, then more compaction is required and processing returns to S300 to prompt the operator to conduct an additional compaction pass and measurement thereafter. If the increase in density is not greater than the threshold, i.e., NO at step S304, then compaction is complete and the operator is informed using display 40 at step S305.

While the methodology has been described relative to one mode or another, it should be recognized that one or more of the modes may be provided simultaneously. For example, the Relative Mode 3 may be provided in conjunction with either one of the Absolute Modes 1 and/or 2. Accordingly, other methodology that provides simultaneous modes may also be used.

VII. CONCLUSION

The above-described invention provides a measurement system to measure material properties in less than 1 minute of elapsed time. The present invention provides a portable lightweight instrument capable of measuring material properties at depths up to 12 inches below the surface without need for penetrating probes. No specialized training is required for operation or licensing required for use, storage, and disposal.

In the previous discussion, it will be understood that the method steps discussed are performed by a processor, such as PU 24 of system 10, executing instructions of program product 40 stored in memory. It is understood that the various devices, modules, mechanisms and systems described herein may be realized in hardware, software, or a combination of hardware and software, and may be compartmentalized other than as shown. They may be implemented by any type of computer system or other apparatus adapted for carrying out the methods described herein. A typical combination of hardware and software could be a general-purpose computer system with a computer program that, when loaded and executed, controls the computer system such that it carries out the methods described herein. Alternatively, a specific use computer, containing specialized hardware for carrying out one or more of the functional tasks of the invention could be utilized. The present invention can also be embedded in a computer program product, which comprises all the features enabling the implementation of the methods and functions described herein, and which—when loaded in a computer system—is able to carry out these methods and functions. Computer program, software program, program, program product, or software, in the present context mean any expression, in any language, code or notation, of a set of instructions intended to cause a system having an information processing capability to perform a particular function either directly or after the following: (a) conversion to another language, code or notation; and/or (b) reproduction in a different material form.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A material analyzer system comprising:
   a sensor; and
   an analyzer unit including:
   an electronic circuit operatively coupled to the sensor for generating an electrical field from the sensor proximate the material; and
   a data analyzer, operatively coupled to the electronic circuit, that determines a compaction indication of the material based on an effect of impedance characteristics of the material on the electrical field,
   wherein the data analyzer corrects the compaction indication for at least a compaction process related inaccuracy in one of a first mode and a second mode of operating the system.

2. The system of claim 1, wherein the electronic circuit includes a sensor circuit for causing the electrical field to transmit from the sensor and a measurement circuit for receiving the electrical field from the material.

3. The system of claim 1, wherein the sensor includes at least one element to transmit an electric field into the material, at least one element to receive an electric field from the material, and at least one element to shape and direct the electric field.

4. The system of claim 1, wherein the electronic circuit generates the electrical field over a set of frequencies that is based on the material.

5. The system of claim 1, wherein the data analyzer includes:
   a measurer configured to control the electronic circuit; and
   a data processor for calculating the compaction indication of the material.

6. The system of claim 1, wherein the data analyzer includes a sensor/mode configurator for determining the mode of operation for the system, wherein the system further includes at least one of the following operating modes:
   the first mode in which the compaction indication includes an accurate absolute density as determined based on a material model;
   the second mode in which the compaction indication includes an estimated absolute density as determined based on an approximated material model; and
   a third mode in which the compaction indication indicates whether further compaction is required based on a percentage of additional compaction achieved compared to a prior compaction pass.

7. The system of claim 6, wherein in the case that the compaction indication is one of the accurate absolute density and the estimated absolute density, the data analyzer corrects a raw density by a correction factor including:
   a compaction process correction term representative of a ratio of each density reading to a relative mean density for a lift of the material; and
   a sensor depth-sensitivity correction term by which a contribution of the sensor at each increment of lift depth must be multiplied to obtain an equal increment contribution.

8. The system of claim 7, wherein the compaction process correction term is calculated based on a compaction process model for determining a mean density of a lift.

9. The system of claim 1, wherein the data analyzer further determines a moisture content of the material based on a material model.

10. The system of claim 1, wherein the data analyzer corrects a raw impedance measurement for contributions of the sensor.

11. The system of claim 1, wherein the compaction process related inaccuracy includes a non-uniform volumetric density profile from the compaction process.

12. The system of claim 1, further comprising a temperature sensor.

13. A method for determining a compaction of a material, the method comprising the steps of:
    measuring an impedance of the material using a sensor;
    determining a compaction indication of the material based on the impedance, wherein the compaction indication includes at least one of an accurate absolute density as determined based on a material model, and an estimated absolute density as determined based on an approximated material model; and correcting the compaction indication with at least a compaction process correction.

14. The method of claim 13, wherein the accurate absolute density is determined in the case that a material model for the material is available.

15. The method of claim 13, further comprising the step of determining whether a material model is available for the material, wherein the material model includes a non-linear multiple variable-parameter estimator for determining an absolute density based on the impedance.

16. The method of claim 15, wherein in the case that the material model for the material is unavailable, the method further comprises the steps of:

querying a user for a material type;
determining whether the material type is valid; and
determining the approximated material model based on a closest material model in the case that the material type is valid.

17. The method of claim 16, wherein in the case that the material type is invalid, further comprising the steps of:

querying a user to run a field Proctor test; and
determining the approximated material model based on a closest material model in the case that the field Proctor test is run.

18. The method of claim 13, wherein the measuring step includes measuring the impedance of the material over a set of frequencies.

19. The method of claim 13, further comprising the step of determining an engineering property of the material other than the compaction indication.

20. The method of claim 19, wherein the engineering property includes at least one of a moisture content and a conductivity.

21. The method of claim 13, wherein the correcting step further includes correcting the compaction indication with a sensor depth-sensitivity correction, wherein the sensor depth-sensitivity correction includes an incremental contribution for a particular sensor at each increment of a lift depth.

22. The method of claim 13, wherein the compaction process correction includes a factor by which each increment reading differs from a relative mean density for an entire lift of the material.

23. The method of claim 13, further comprising the step of correcting the impedance for contributions of the sensor.

24. A computer program product comprising a computer useable medium having computer readable program code embodied therein for determining a compaction indication of a material, the program product comprising:

program code configured to measure an impedance of the material based on a reading by a sensor; and
program code configured to determine a compaction indication of the material based on the impedance, wherein the compaction indication includes at least one of an accurate absolute density as determined based on a material model and an estimated absolute density as determined based on an approximated material model, and wherein the compaction indication is corrected using at least a compaction process correction.

25. The program product of claim 24, wherein the determining program code determines the accurate absolute density in the case that a material model for the material is available and the estimated absolute density in the case that the material model for the material is unavailable.

26. The program product of claim 24, wherein in the case that the material model for the material is unavailable, the determining program code further:

queries a user for a material type;
determines whether the material type is valid; and
determines the approximated material model based on a closest material model in the case that the material type is valid.

27. The program product of claim 26, wherein in the case that the material type is invalid, the determining program code further:

queries a user to run a field Proctor test; and
determines the approximated material model based on a closest material model in the case that the field Proctor test is run.

28. The program product of claim 24, wherein the determining program code includes a non-linear multiple variable-parameter estimator for determining an absolute density based on the impedance.

29. The program product of claim 24, wherein the measuring program code measures the impedance of the material at a plurality of frequencies.

30. The program product of claim 24, wherein the determining program code further determines an engineering property of the material other than the compaction indication.

31. The program product of claim 30, wherein the engineering property includes at least one of a moisture content and a conductivity.

32. A material analyzer system comprising:

a sensor; and
an analyzer unit including:
an electronic circuit operatively coupled to the sensor for generating an electrical field from the sensor proximate the material; and
a data analyzer, operatively coupled to the electronic circuit, that determines a property of the material by implementing a material model capable of determining the property based on an effect of impedance characteristics of the material on the electrical field,
wherein the material model implements a non-linear multiple variable-parameter estimator.

* * * * *

UNITED STATES PATENT AND TRADEMARK OFFICE
CERTIFICATE OF CORRECTION

| | |
|---|---|
| PATENT NO. | : 7,219,024 B2 |
| APPLICATION NO. | : 11/127391 |
| DATED | : May 15, 2007 |
| INVENTOR(S) | : Gamache et al. |

Page 1 of 1

It is certified that error appears in the above-identified patent and that said Letters Patent is hereby corrected as shown below:

Column 11, Line 13, Delete "estabilished" and insert --established--.
Column 16, Line 67, Delete "S11" and insert --S10--.
Column 17, Line 59, Delete "S1105" and insert --S105--.

Signed and Sealed this

Fourteenth Day of August, 2007

JON W. DUDAS
*Director of the United States Patent and Trademark Office*